United States Patent
Wong et al.

(10) Patent No.: US 9,532,840 B2
(45) Date of Patent: Jan. 3, 2017

(54) SLIDER CONTROL OF CATHETERS AND WIRES

(71) Applicant: Hansen Medical, Inc.

(72) Inventors: Serena H. Wong, Mountain View, CA (US); Sean P. Walker, Fremont, CA (US); June Park, Palo Alto, CA (US); Richard Henderson, Fremont, CA (US)

(73) Assignee: HANSEN MEDICAL, INC., Mountain View, CA (US)

(*) Notice: Subject to any disclaimer, the term of this patent is extended or adjusted under 35 U.S.C. 154(b) by 295 days.

(21) Appl. No.: 14/201,582

(22) Filed: Mar. 7, 2014

(65) Prior Publication Data

US 2014/0257334 A1 Sep. 11, 2014

Related U.S. Application Data

(60) Provisional application No. 61/774,690, filed on Mar. 8, 2013.

(51) Int. Cl.
| | |
|---|---|
| *G05B 19/00* | (2006.01) |
| *B25J 15/02* | (2006.01) |
| *A61B 19/00* | (2006.01) |

(52) U.S. Cl.
CPC .......... *A61B 19/2203* (2013.01); *A61B 34/30* (2016.02); *A61B 34/74* (2016.02); *A61B 34/76* (2016.02); *A61B 2034/301* (2016.02)

(58) Field of Classification Search
CPC ... A61B 17/00; A61B 17/1628; A61B 5/0077; A61B 17/12118; A61B 1/0016; A61B 5/0538; G06T 7/0012; G06T 2219/2016; G06T 2210/28; G06T 2210/41; A61G 2203/12; A61G 2007/0509; A61G 2007/051; A61G 2203/16; A61M 25/0105
See application file for complete search history.

(56) References Cited

U.S. PATENT DOCUMENTS

| | | | |
|---|---|---|---|
| 5,398,691 | A | 3/1995 | Martin et al. |
| 5,408,409 | A | 4/1995 | Glassman et al. |
| 5,524,180 | A | 6/1996 | Wang et al. |
| 5,631,973 | A | 5/1997 | Green |
| 5,713,946 | A | 2/1998 | Ben-Haim |
| 5,749,362 | A | 5/1998 | Funda et al. |
| 5,859,934 | A | 1/1999 | Green |
| 5,876,325 | A | 3/1999 | Mizuno et al. |

(Continued)

FOREIGN PATENT DOCUMENTS

| | | |
|---|---|---|
| WO | 03086190 A1 | 10/2003 |
| WO | 2006099056 A2 | 9/2006 |

OTHER PUBLICATIONS

EnSite Velocity Cardiac Mapping System, http://www.sjmprofessional.com/Products/US/Mapping-and-Visualization/EnSite-Velocity.aspx.

(Continued)

*Primary Examiner* — Marlon Fletcher
(74) *Attorney, Agent, or Firm* — Dorsey & Whitney LLP

(57) ABSTRACT

One exemplary user interface for a medical robotics system may include a control panel and one or more sliders that may be slidably carried by the control panel to actuate one or more motors for moving a surgical instrument of the medical robotics system. The sliders may be configured to actuate the motors to move the surgical instrument along a respective one of a plurality of degrees of freedom.

20 Claims, 5 Drawing Sheets

(56) References Cited

U.S. PATENT DOCUMENTS

| | | | |
|---|---|---|---|
| 5,951,475 | A | 9/1999 | Gueziec et al. |
| 6,226,543 | B1 | 5/2001 | Gilboa et al. |
| 6,259,806 | B1 | 7/2001 | Green |
| 6,272,371 | B1 | 8/2001 | Shlomo |
| 6,424,885 | B1 | 7/2002 | Niemeyer et al. |
| 6,545,760 | B1 | 4/2003 | Froggatt et al. |
| 6,726,675 | B1 | 4/2004 | Beyar |
| 7,151,527 | B2 * | 12/2006 | Culver ............... G06F 3/016 345/156 |
| 7,155,315 | B2 | 12/2006 | Niemeyer et al. |
| RE42,183 | E * | 3/2011 | Culver ............... G06F 3/0362 345/157 |
| 8,137,279 | B2 * | 3/2012 | Taylor ................. A61B 8/08 600/459 |
| 8,460,236 | B2 | 6/2013 | Roelle et al. |
| 9,039,685 | B2 | 5/2015 | Larkin et al. |
| 2006/0013523 | A1 | 1/2006 | Childlers et al. |
| 2006/0025676 | A1 | 2/2006 | Viswanathan et al. |
| 2006/0095022 | A1 * | 5/2006 | Moll .................... A61B 8/12 606/1 |
| 2006/0100610 | A1 * | 5/2006 | Wallace ........... A61B 19/2203 606/1 |
| 2007/0013336 | A1 | 1/2007 | Nowlin et al. |
| 2007/0043338 | A1 * | 2/2007 | Moll ................. A61B 19/2203 606/1 |
| 2007/0135803 | A1 | 6/2007 | Belson |
| 2007/0197896 | A1 * | 8/2007 | Moll ................. A61B 1/00039 600/407 |
| 2007/0265503 | A1 | 11/2007 | Schlesinger et al. |
| 2008/0183193 | A1 * | 7/2008 | Omori ................... A61B 17/29 606/130 |
| 2008/0212082 | A1 | 9/2008 | Froggatt et al. |
| 2008/0218770 | A1 | 9/2008 | Moll et al. |
| 2008/0285909 | A1 | 11/2008 | Younge et al. |
| 2009/0137952 | A1 | 5/2009 | Ramamurthy et al. |
| 2009/0245600 | A1 * | 10/2009 | Hoffman ........... A61B 1/00039 382/128 |
| 2009/0248036 | A1 * | 10/2009 | Hoffman ........... A61B 19/2203 606/130 |
| 2009/0262109 | A1 | 10/2009 | Markowitz et al. |
| 2010/0114115 | A1 | 5/2010 | Schlesinger et al. |
| 2010/0225209 | A1 * | 9/2010 | Goldberg ...................... 312/209 |
| 2010/0228249 | A1 * | 9/2010 | Mohr ................. A61B 19/2203 606/41 |
| 2013/0172906 | A1 * | 7/2013 | Olson ................. A61B 19/2203 606/130 |
| 2014/0243849 | A1 * | 8/2014 | Saglam ................... A61B 18/22 606/130 |
| 2014/0257334 | A1 * | 9/2014 | Wong ................. A61B 19/2203 606/130 |
| 2015/0054753 | A1 * | 2/2015 | Morgan ............... A61B 17/068 345/173 |
| 2015/0100066 | A1 * | 4/2015 | Kostrzewski ........ A61B 19/201 606/130 |

OTHER PUBLICATIONS

Duncan, "Sensing Shape—Fiber-Bragg-Grating Sensor Arrays Monitor Shape at High Resolution," SPIE's OE Magazine, Sep. 2005, pp. 18-21.

Froggatt et al., "High-spatial-resolution distributed strain measurement in optical fiber with Rayleigh scatter," Applied Optics, Apr. 1, 1998, pp. 1735-1740, vol. 37, No. 10.

* cited by examiner

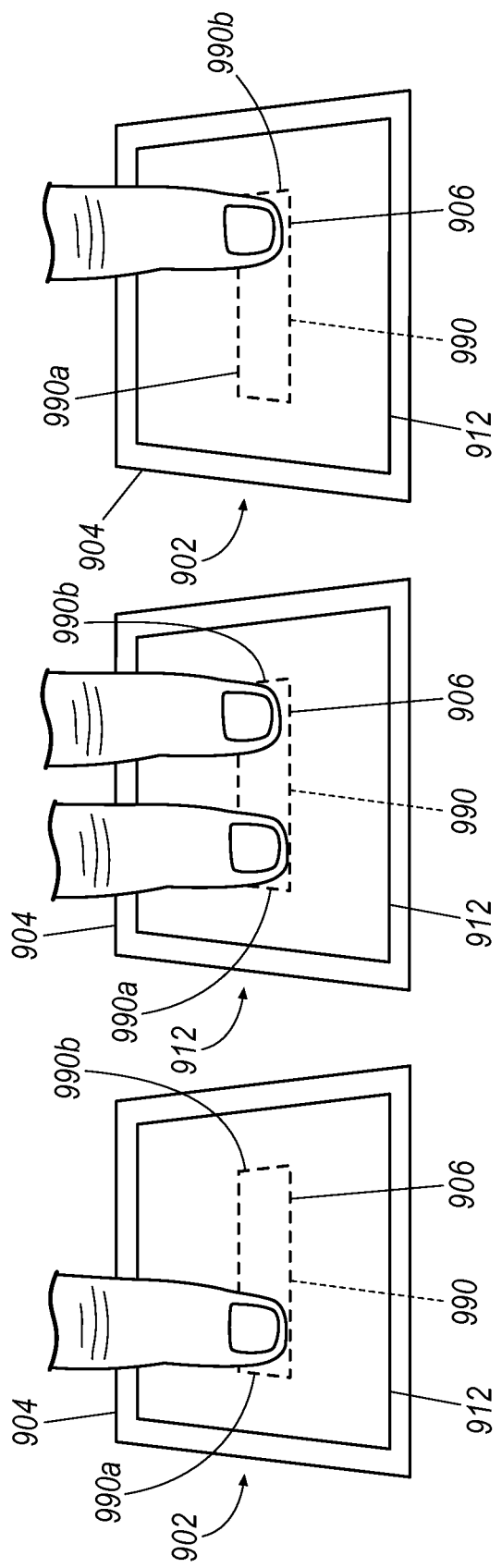

SLIDER CONTROL OF CATHETERS AND WIRES

CROSS-REFERENCE TO RELATED APPLICATIONS

This application claims priority to U.S. Provisional Patent Application No. 61/774,690, filed Mar. 8, 2013, the contents of which are hereby incorporated in their entirety.

BACKGROUND

Medical robotics manufacturers are developing user interfaces to effectively perform various robot-assisted surgical procedures. The user interfaces may be operated to control robotic catheters and wires in vascular procedures, or the user interfaces may be integrated within other robotic systems to control other suitable devices to perform various surgical procedures. One exemplary user interface may include a joystick device, which can be used to simultaneously control movement of a surgical device with multiple degrees of freedom. Depending on the procedure and the subjective preference of the physician performing the procedure, this joystick may not be considered intuitive or otherwise desirable.

Therefore, a need exists for an improved user interface for a medical robotics system that provides independent and intuitive control of multiple degrees of freedom of surgical instruments.

SUMMARY

One example of a user interface for a medical robotics system may include a control panel and one or more sliders that may be slidably carried by the control panel to actuate one or more motors for moving a surgical instrument of the medical robotics system. The sliders may be configured to actuate the motors to move the surgical instrument along a respective one of a plurality of degrees of freedom.

BRIEF DESCRIPTION OF THE DRAWINGS

FIG. 9 is a schematic view of still another example of the user interface of FIG. 1, with the user interface including a touchscreen device configured to actuate a motor to move a catheter in response to two fingers alternating contact with the touchscreen device with a predetermined distance between the fingers being used to move the catheter tip an associated distance.

DETAILED DESCRIPTION

Figure 1:
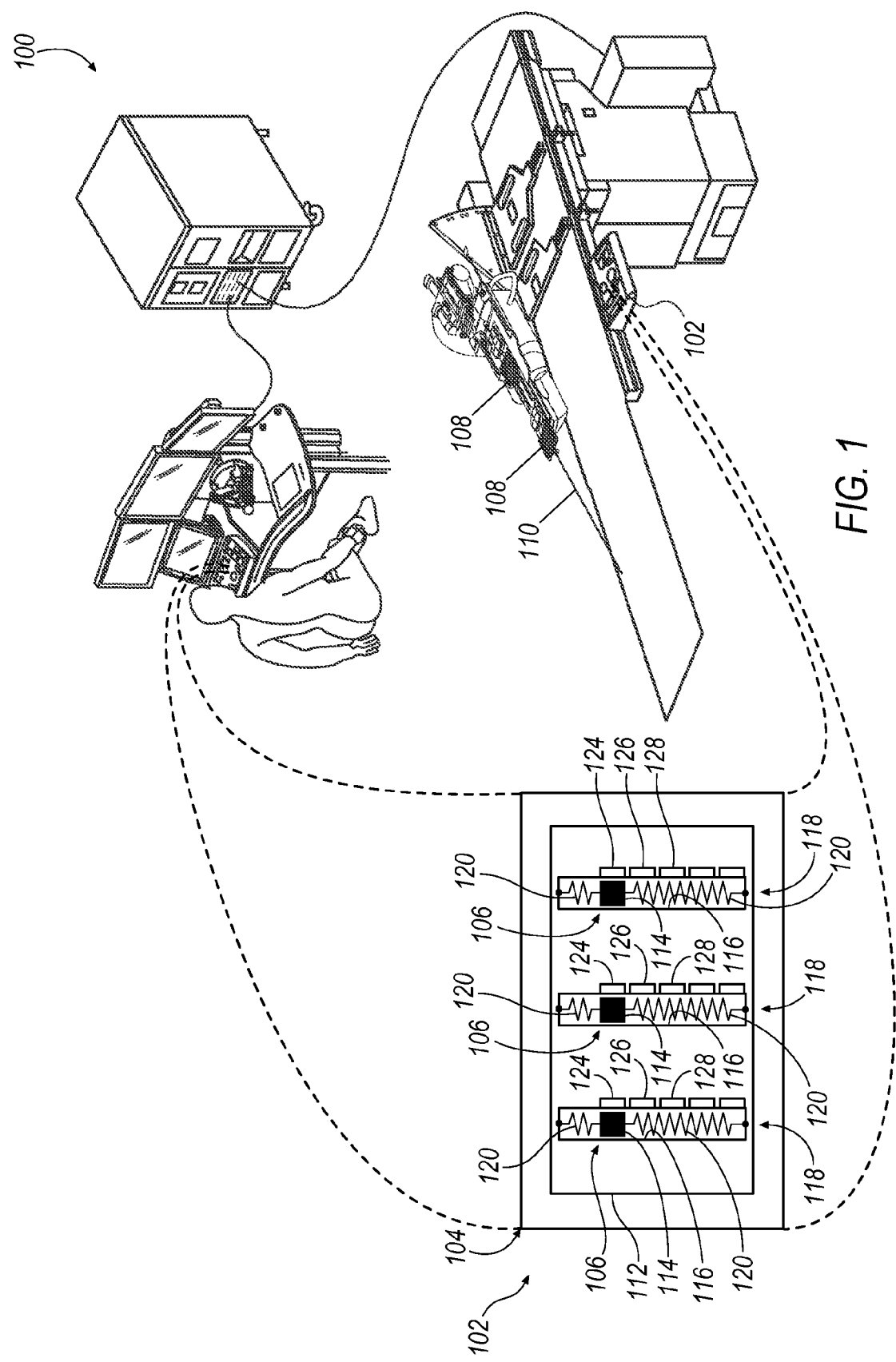
FIG. 1 is a schematic view of one example of a user interface for a medical robotics system having a plurality of sliders movable along linear paths that are arranged parallel to one another.

Referring now to the discussion that follows and also to the drawings, illustrative approaches are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Referring to FIG. 1, one example of a user interface 102 for a medical robotics system 100 may include a control panel 104 and a plurality of sliders 106, which are slidably carried by the control panel to actuate one or more motors 108 for moving a surgical instrument 110 of the system. The sliders 106 can move the surgical instrument along a respective one of a plurality of degrees of freedom. In this respect, each slider 106 may be operated to control movement of the surgical instrument exclusively along one degree of freedom, independent of the remaining degrees of freedom controlled by the remaining sliders. As one example, the user interface 102 may be utilized for controlling a catheter 110 and wire for a robotic catheter control system. However, the user interface 102 may be used for other suitable medical robotics systems. The control panel 104 may be a housing 112 that may slidably carry the sliders 106, with tongue 114 in groove 116 attachments or outer suitable couplings. In another example shown in FIG. 4, the control panel 404 may be a touchscreen device 412 that provides virtual sliders 406.

Each slider may control an independent degree of free movement of the surgical instrument. For example, one slider may be adapted for controlling only the insertion/retraction of the surgical instrument. Another slider may be adapted for controlling only the rolling or rotation of the surgical instrument. For instance, the slider may actuate one or more motors to pivot a catheter tip about a longitudinal axis of the catheter. Still another slider may be adapted for controlling only the articulation or bending movement of the surgical instrument within a bending plane.

Figure 2:
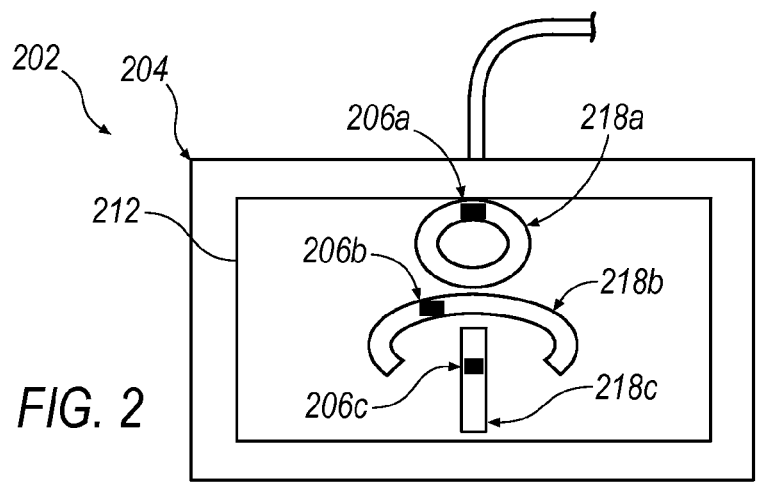
FIG. 2 is a schematic view of another example of the user interface of FIG. 1, with the user interface including sliders movable along one or more non-linear paths.
Figure 3:
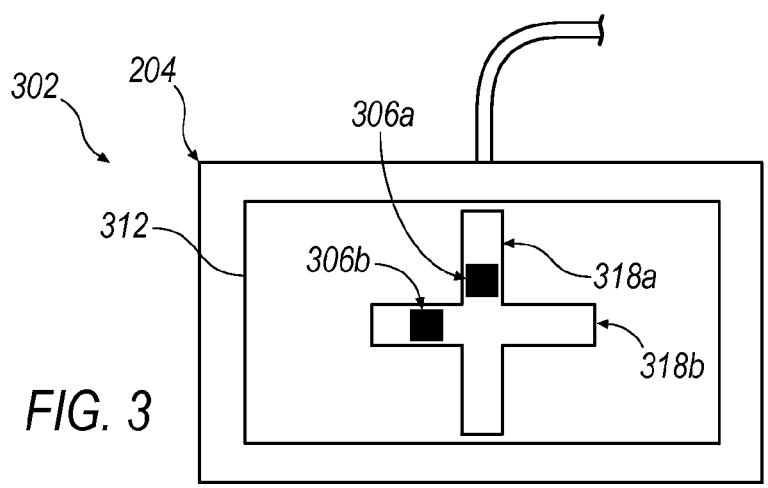
FIG. 3 is a schematic view of still another example of the user interface of FIG. 1, with the user interface including a pair of sliders movable along paths that are perpendicular to one another.

The sliders may have a predetermined shape or orientation with respect to each other, or be arranged in a layout or combination, which permits control of the surgical instrument to be more intuitive. As one example, FIG. 1 illustrates one example of a user interface 102 having a plurality of sliders 106 movable along a plurality of linear paths 118, which may be arranged parallel with respect to one another. As exemplified in FIG. 2, another example of a user interface 202 may include a roller slider 206a, which may be movable along a round or elliptical path 218a on the control panel 204 so as to permit intuitive control over a rolling or rotational movement of the surgical instrument. This user interface 202 may further include an articulation slider 206b, which may be movable along a curved or arcuate path 218b on the control panel so as to control an articulation or bending of the surgical instrument. Further, this user interface 202 may have an insertion/retraction slider 206c, which may be movable along a linear path 218c to control an insertion or refraction of the surgical instrument into the body of a patient. However, any one or more of these paths can have circular, elliptical, parabolic or other non-linear shapes based on, for example, the actual movement of the instrument so as to provide intuitive operation of the catheter. Exemplary illustrations of these paths and the associated movement of the catheter are shown in FIGS. 2-5. Turning now to FIG. 3, another example of a user interface 302 may include an insertion/retraction slider 306a, which may be movable along a linear insertion path 318a so as to control the insertion and retraction of the surgical instrument with respect to the body of the patient. The user interface 302 may also have an articulation slider 306b, which may be movable along a linear articulation path 318b for controlling an articulation of the surgical instrument within a bending plane. The linear articulation path may be perpendicular to the linear insertion path to, for example, provide intuitive control of the surgical instrument. Of course, however, it is contemplated that any one or more sliders that may be movable along paths may have other suitable shapes with various orientations with respect to each other.

The orientation and shape of a slider can be used to convey the meaning of the control. For instance, while parallel sliders (e.g., as shown in FIG. 1) can be used to control different degrees of freedom, another exemplary user interface may include the articulation slider disposed perpendicular to the insertion slider to convey motion in an orthogonal direction (e.g., as shown in FIG. 3). Sliders can also be straight, curved or otherwise shaped in a particular way to make it more intuitive for a given degree of freedom (e.g., as shown in FIG. 2). For instance, the articulation slider can be curved similar to the maximum extent of the articulation. Roll of the instrument may be controlled by a slider movable along a circular path (e.g., as shown in FIG. 2).

The sliders may be configured to control movement of the surgical instrument along the related degree of freedom by utilizing various modes of control, including velocity control, relative position control and absolute position control. Velocity control is a mode of control in which the position of the slider will command a rate of change of a degree of freedom of the catheter. For example, the position of one slider, which is utilized to exclusively control catheter insertion and retraction, may be mapped to the proportional velocity of the catheter or wire and provide a maximum catheter velocity, based on a maximum speed of insertion or retraction capable of being provided by the motors, a safety threshold to protect the patient from high-velocity catheter movements, or various other factors.

Furthermore, relative position control is a mode of control in which the position of the slider will command the change in position of a degree of freedom of the catheter relative to a starting position. In one example the slider could move freely without changing the catheter insertion until a button on the slider was pressed, at which point the change in slider position with respect to the position of initial button press would command a similar change in position of the catheter. A slider may be mapped to the relative position driving for finer control of catheter or wire motions when the response is delayed. As one example, one slider, which is utilized to exclusively control wire rolling, may be mapped to control the relative wire roll as the physician operates the slider to roll the wire by a predetermined degree. The change in slider position indicates to the physician the expected amount of roll change in the wire and thereby allows the physician to stop rolling the wire and avoid an associated whipping action of the twisted wire when the actual wire roll did not match the predetermined roll degree due to the buildup along the wire.

Moreover, a slider may be mapped to the absolute position of the catheter or wire. Absolute position control is a mode of control in which the position of the slider directly maps to a position of a degree of freedom of the catheter. For instance, one slider, which may be utilized for exclusively controlling catheter articulation, may be mapped to the absolute amount of articulation of the catheter to, for example, alert the physician of an articulated position of the catheter and prevent any articulated catheter from being inserted or retracted through a passage not sufficiently shaped for passing the articulated catheter.

One or more of the control modes may be accomplished by one or more springs, friction hold mechanisms, force feedback mechanisms, potentiometers, optical/magnetic encoders, other suitable mechanisms or any combination thereof. For instance, each slider 106 may be coupled to one or more springs 120 (e.g., as shown in FIG. 1) to move the sliders to a position. In particular, the sliders 106 can have spring return to a zero position, in which case velocity control (analog or binary) should be used. Sliders 106 can also have a friction hold configured to maintain a position of the sliders 106 upon release of the slider by the user, which may be more advantageous for controls of an absolute position or relative position of the surgical instrument. To that end, one or more of the sliders 106 may be coupled to a friction hold mechanism 122 for absolute position or relative position. For example, a resilient or deformable material may be sandwiched between the tongue and groove. However, a variety of other suitable friction hold mechanisms may be utilized. Furthermore, one or more sliders may be coupled to force feedback mechanisms 124 to provide mechanical feedback or one or more detent forces for control. Moreover, one or more sliders may include a potentiometer 126, optical encoder 128 or magnetic encoder, for example.

In one exemplary approach, a single slider can exist for each degree of freedom, which can be particularly useful in position control because each slider can keep its value of command and retain that visually for the user to serve as a visual cue. This could be particularly useful in the case of articulation when, for example, the physician may fail to relax the bend of the catheter as the catheter is tracking over a guide wire. Thus, the slider can provide a visual indication of how much the catheter is articulated, which can alert the physician to relax the bend.

Figure 4:
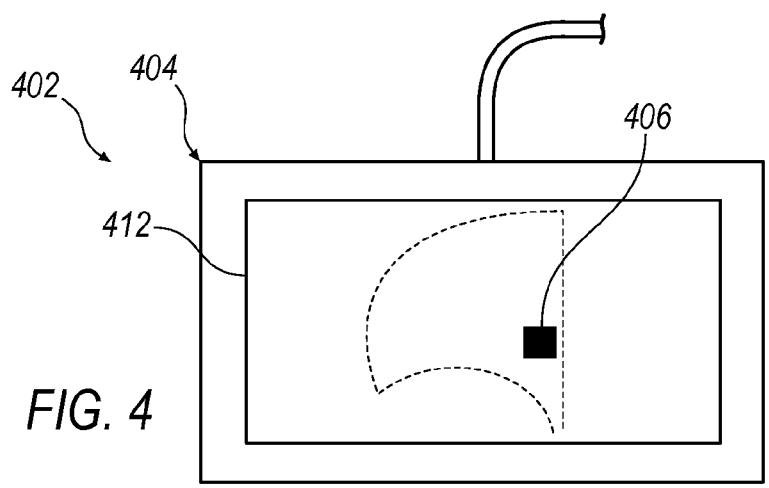
FIG. 4 is a schematic view of yet another example of the user interface of FIG. 1, with the user interface including a touchscreen device.

As shown in FIG. 4, one exemplary touchscreen device 412 can include a virtual slider 406 having multiple paths in order to map multiple degrees of freedom at once or imply certain combinations of degrees of freedom that are valid. For instance, the work space of the leader acquires a particular shape based on its insertion value because the exposed length of its articulation section changes. This can be mapped to a 2D plane. The plane can be open as drawn with freedom to move the slider 406 within the open space, as indicated by the dotted line closure. The plane could also have a dynamic boundary that could change to limit different areas as the procedure progresses. Alternatively, the plane could be separated into individual virtual tracks or sliders that may imply the steps needed to get from one distinct combination to another. This could be particularly useful if the control requires movement through a certain set of states.

Sliders may move in 2D in the cardioid shape, representing the area of insertion past the sheath and its relationship to articulation. The 2D plane represents all possible combinations of insertion and articulation. There are variations on all of these slider combinations. These sliders can be large and encompass the entire pendant or controller. Another option is to combine them with other input devices such as joysticks or thumbwheels. They can be a component of the joystick, for example placed on the top of the joystick. Conversely, the joystick or thumbwheel can be placed on top of a slider.

Figure 5:
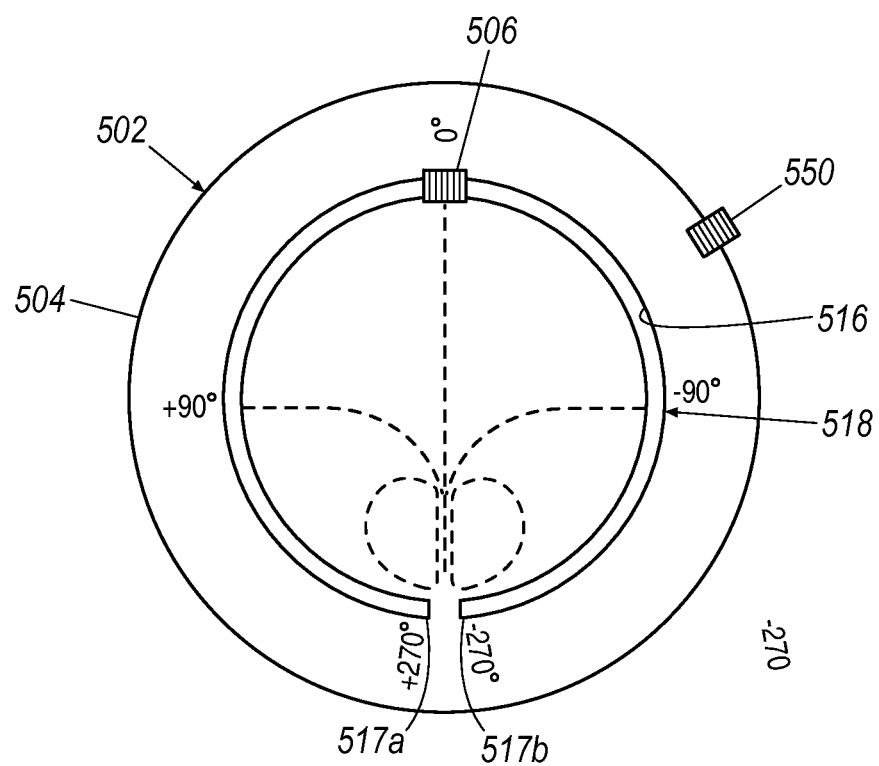
FIG. 5 is an elevation view of another example of the user interface of FIG. 1, with the user interface including a roller mechanism and a slider movable along an arcuate path.

Referring now to FIG. 5, another example of a user interface 502 is similar to the user interface 102 of FIG. 1. The user interface 502 includes features, which are similar to those of the user interface 102 and are identified by similar reference numerals in the 500 series. However, while the user interface 102 may include three sliders 106, which are slidably carried by the housing 112 of the control panel 104 and are movable along a respective one of three linear paths 118, the user interface 502 includes only one slider 506 that is slidably carried by a control panel 504 and is movable along one arcuate path 518. In particular, the housing 512 may have an arcuate groove 516 or rail. The groove 516 may have opposing ends 517*a*, 517*b*, and the slider 506 is configured to move along the groove 516 between the opposing ends 517*a*, 517*b* so as to control an articulation of a tip of the catheter within a bending plane. In particular, the slider 506 can be moved to a center portion of the groove 516 that is equidistant from the opposing ends 517*a*, 517*b* so as to actuate one or more motors to move the catheter tip to zero degrees of articulation. The slider 506 may be further configured to actuate the motor to articulate the catheter tip up to 270 degrees in one direction in response to the slider 506 being moved from the center portion 519 to one end 517*a* of the arcuate groove 516. Similarly, the slider 506 may be configured to actuate the motor to articulate the catheter tip up to 270 degrees in an opposite direction in response to the slider 506 being moved from the center portion 519 to the other end 517*b* of the arcuate groove 516. The slider can be configured to bend the catheter tip to maximum articulation that is more or less than 270 degrees.

The user interface 502 can further include a roller mechanism 550 that is configured to actuate a motor to insert or retract the catheter. In particular, the rolling mechanism 550 is rotatably carried by the control panel 504. The roller mechanism 550 is configured to insert the catheter in response to a physician rolling the roller mechanism 550 in one direction and retracts the catheter in response to the physician rolling the roller mechanism 550 in the opposite direction. Another exemplary illustration of the roller mechanism can be configured to actuate a motor to rotate or roll the catheter. This rolling mechanism can be configured to actuate the motor so as to roll the catheter by rotating the catheter tip about a longitudinal axis of the catheter from, for example, a first bending plane to a second bending plane. In this respect, the user interface 502 may be used to, for example, physically rotate the catheter within a blood vessel and provide a rolling motion of the tip, thus rotating the bending plane of the catheter tip. The roller mechanism 550 can be further configured to reassign articulation direction of the slider 516, such that the slider 516 is configured to articulate the catheter tip within a bending plane defined by the roller mechanism.

Figure 6:
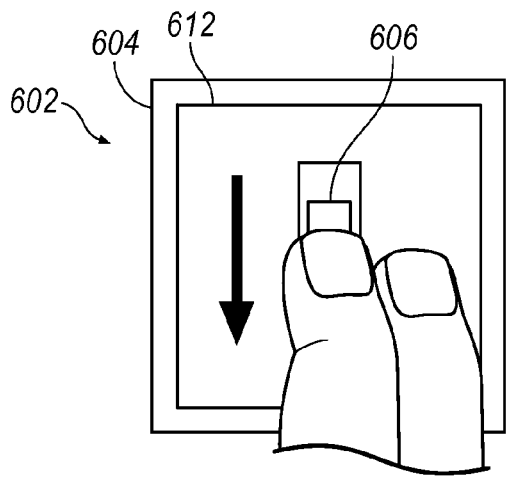
FIG. 6 is a schematic view of still another example of the user interface of FIG. 1, with the user interface including a touchscreen device configured to actuate a motor to move a catheter in response to simultaneous two-finger contact with the touchscreen device to operate the same.

Referring now to FIG. 6, another example of a user interface 602 includes a touchscreen device 612, which is similar to the touchscreen device 412 of FIG. 4. However, while the touchscreen device 412 may be configured to be operated by only one finger, the touchscreen device 612 is configured to actuate one or more motors to move a catheter tip in response to at least two fingers simultaneously operating a virtual slider 606 or other virtual control provided by the touchscreen device 612. As another example, the touchscreen device 612 can be configured to actuate the motor to move the catheter tip, in response to a double finger tap on the touchscreen device preceding the use of one finger to operate the touchscreen device 612. The use of a double finger tap may act as a safety mechanism which prevents accidental actuation of the surgical instrument in response to a user accidentally bumping or brushing the user interface 602.

Figure 7:
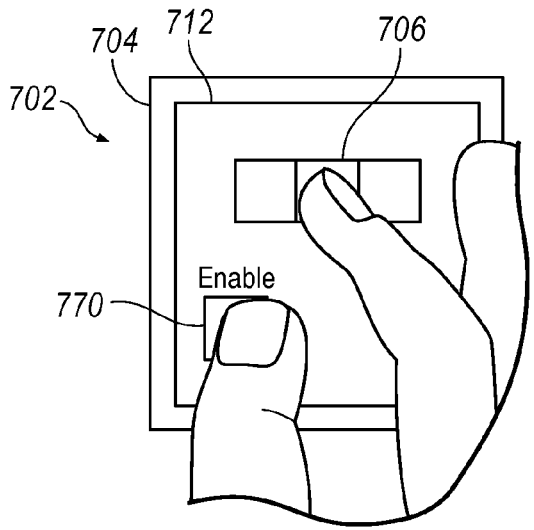
FIG. 7 is a schematic view of another example of the user interface of FIG. 1, with the user interface including a touchscreen device configured to actuate a motor to move a catheter in response to one finger pressing and holding an activation surface portion and another finger simultaneously operating the touchscreen device.

Referring now to FIG. 7, yet another example of the user interface 702 includes a touchscreen device 712 and is similar to the user interface 602 of FIG. 6 having the touchscreen device 612 of FIG. 6. However, the touchscreen device 712 can have an activation surface portion 770 configured to activate the touchscreen device 712, such that a user may operate a virtual slider 706 on the touchscreen device 712, in response to one finger pressing and holding the activation surface portion 770 and another finger simultaneously operating one or more virtual sliders 706 on the touchscreen device 712. Conversely, when the finger is removed from the activation surface portion 770, the touchscreen device 712 is deactivated, such that the virtual sliders 706 cannot be operated to actuate the motor and articulate the catheter tip. In this manner, activation surface portion 770 acts as a safety mechanism which prevents accidental actuation of the surgical instrument in response to a user accidentally bumping or brushing the virtual slider 706 unless the activation surface portion 770 is also engaged or activated.

Figure 8:
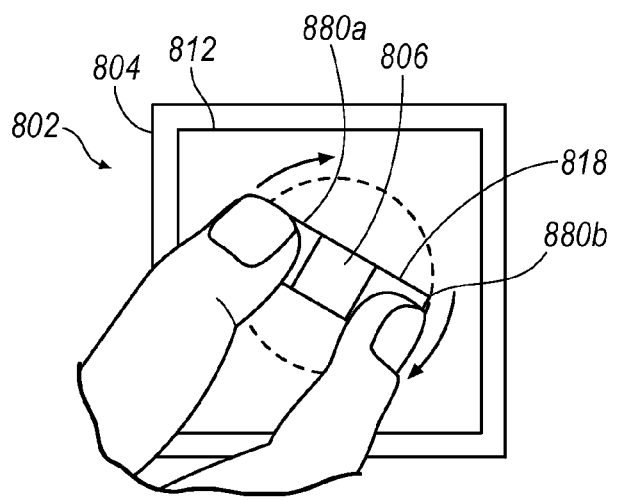
FIG. 8 is a schematic view of yet another example of the user interface of FIG. 1, with the user interface including a touchscreen device configured to actuate a motor to move a catheter in response to two fingers rotating the virtual slider.

With attention to FIG. 8, still another exemplary illustration of a user interface 802 having a touchscreen device 812 is similar to the user interface 602 of FIG. 6 having the touchscreen device 612. However, the touchscreen device 812 includes a virtual slider 806 that is configured to move along a linear path 818 to actuate a motor so as to articulate a catheter tip within a bending plane. Moreover, the linear path 818 may be rotated in response to two fingers holding opposing ends 880*a*, 880*b* of the linear path 818, so as to actuate a motor to rotate the catheter tip about a longitudinal axis of the catheter. Alternatively, the linear path 818 may be rotated so as to rotate the plane of bending of articulation, which is defined by the linear path 818 corresponding to the rotation of the linear path. For example, the physician may rotate the linear path so as to translate or revolve the catheter tip around a bending point in the catheter that is spaced apart from the catheter tip, without causing the catheter tip to actually rotate or spin on an axis extending through the tip. Still another exemplary user interface may include a control panel having a hand-operated mechanical slider, which is slidably carried along a groove or rail formed on a carrier, which is in turn rotatably attached to a control panel. In this respect, the motor can rotate or roll the bending plane in response to a physician rotating the carrier. The motor can articulate or bend the catheter tip within the bending plane, as defined by the rotational position of the carrier, in response to the slider being moved along the groove.

Turning now to FIG. 9, another example of a user interface 902 includes a touchscreen device 912 having a virtual slider 906 and is similar to the user interface 602 of FIG. 6. However, the touchscreen device 912 is configured to move the catheter tip in response to a finger contacting a portion of the virtual slider 906 so as to actuate a motor to move the catheter tip to a position mapped to that portion of the virtual slider 906. The touchscreen device 912 may be further configured to cause rapid alternation of commands by using two fingers to simultaneously contact spaced apart portions 990a, 990b of the virtual slider 906 in a rocking manner. In particular, while the virtual slider 606 of FIG. 6 is configured to be operated in response to a finger sliding an image across the touchscreen 612, the virtual slider 906 of the touchscreen device 912 can be a surface area portion 990 of the touchscreen device 912, within which the fingers can alternate contact with spaced apart portions 990a 990b of the touchscreen device 912. The surface area portion 990 can display an image extending between the spaced apart portions 990a, 990b, such as a line and an associated measurement, such as position or speed. Moreover, the surface area portion 990 can display an image traveling between the spaced apart portions 990a, 990b. However, the touchscreen device 912 can display various other images or no images at all depending upon, for example, the surgical procedure to be performed or the preferences of the physician performing the procedure. The surface area portion 990 can provide a predetermined surface area of the touch screen device 912 that is configured to actuate the motor for moving the catheter tip based on, for example, the distance between the points of the touch screen device contacted by the fingers, e.g. spaced apart portions 990a, 990b. By way of another example, the catheter tip may be moved only when contact with the virtual slider 906 is alternated between end portions 990a, 990b of the virtual slider 906 within a predetermined period of time. In this manner, the catheter tip is moved only in response to the alternating movement, and thereby decreases opportunities for accidental movement of the catheter tip.

The exemplary systems and components described herein, including the various exemplary user interface devices, may include a computer or a computer readable storage medium implementing the operation of drive and implementing the various methods and processes described herein. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many examples and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed as new and desired to be protected by Letters Patent of the United States is:

1. A user interface configured to receive user input commands for a medical robotics system, the user interface comprising:
   a control panel; and
   a plurality of sliders slidably carried by the control panel to control actuation of at least one drive motor, for moving a surgical instrument of the medical robotics system;
   wherein each of the plurality of sliders controls movement of the surgical instrument along a respective one of a plurality of degrees of freedom, and
   wherein the user interface is communicatively coupled to, but physically remote from, the at least one drive motor and the surgical instrument.

2. The user interface of claim 1, wherein the control panel is a touchscreen device.

3. The user interface of claim 1, wherein at least one of the plurality of sliders is coupled to a spring for moving the sliders toward a position.

4. The user interface of claim 1, wherein at least one of the plurality of sliders includes a friction hold mechanism.

5. The user interface of claim 1, wherein at least one of the plurality of sliders includes at least one force feedback mechanism.

6. The user interface of claim 5, wherein at least one force feedback mechanism provides one or more detent forces.

7. The user interface of claim 1, wherein the plurality of sliders comprises:
   a rolling slider controlling a rolling movement of the surgical instrument within a portion of a body of a patient, the rolling slider being movable along at least one of a circular path and an elliptical path.

8. The user interface of claim 1, wherein the plurality of sliders comprises:
   an articulation slider controlling an articulation of the surgical instrument within a portion of a body of a patient, the articulation slider being movable along an arcuate path.

9. The user interface of claim 1, wherein the plurality of sliders comprises at least one of:
   an insertion slider controlling at least one of an insertion and a retraction of the surgical instrument into a portion of a body of a patient, the insertion slider being movable along at least one of a linear insertion path and a non-linear path;
   an articulation slider controlling an articulation of the surgical instrument within a portion of a body of a patient, the articulation slider being movable along at least one of a linear insertion path and a non-linear path; and
   a rolling slider controlling a rolling movement of the surgical movement within a portion of a body of a patient, the rolling slider being movable along at least one of a linear insertion path and a nonlinear path.

10. The user interface of claim 1, wherein the plurality of sliders comprises:
    an insertion slider movable along a linear insertion path for controlling an insertion of the surgical instrument into a portion of a body of a patient; and
    an articulation slider movable along a linear articulation path for controlling an articulation of the surgical instrument within the portion of the body of the patient,
    wherein the linear articulation path is perpendicular to the linear insertion path.

11. A user interface configured to receive user input commands for a medical robotics system, the user interface comprising:
    a control panel; and
    at least one slider slidably carried by the control panel to control actuation of at least one drive motor, for moving a catheter of the medical robotics system;
    wherein the at least one slider controls movement of the catheter along at least one degree of freedom, and
    wherein the user interface is communicatively coupled to, but physically remote from, the at least one drive motor and the catheter.

12. The user interface of claim 11, wherein the control panel includes an arcuate groove, and the at least one slider is movable along the arcuate groove and configured to control an articulation of a tip of the catheter within one bending plane.

13. The user interface of claim 12, wherein the at least one slider is configured to actuate the at least one drive motor to dispose the catheter at zero degrees of articulation, in response to the at least one slider being moved to a center portion along the arcuate groove.

14. The user interface of claim 13, wherein the arcuate groove has a pair of ends, and wherein the at least one slider is configured to actuate the at least one drive motor to articulate the catheter in one direction in response to the at least one slider moving from the center portion to one end of the arcuate groove.

15. The user interface of claim 11, further comprising:
    a roller mechanism rotatably carried by the control panel, wherein the roller mechanism is configured to actuate the at least one drive motor to articulate the catheter within a bending plane.

16. The user interface of claim 11, wherein the control panel is a touchscreen device configured to actuate the at least one drive motor to move the catheter, and wherein the touchscreen device has an activation surface portion configured to activate the touchscreen device and permit operation of the catheter in response to one finger pressing and holding the activation surface portion and another finger simultaneously operating the touchscreen device.

17. The user interface of claim 11, wherein the control panel is a touchscreen device configured to actuate the at least one drive motor to move the catheter, and wherein the touchscreen device is configured to permit operation of the catheter in response to at least two fingers simultaneously operating the touchscreen device.

18. The user interface of claim 11, wherein the control panel is a touchscreen device configured to actuate the at least one drive motor to move the catheter, and wherein the touchscreen device is configured to activate the touchscreen device and permit operation of the catheter in response to a double finger tap preceding operation of the touchscreen device.

19. A medical robotics system, comprising:
 a surgical instrument;
 at least one drive motor physically coupled to the surgical instrument; and
 a user interface communicatively coupled to, but physically remote from, the at least one drive motor and the surgical instrument;
 wherein the user interface includes a control panel and at least one slider slidably carried by the control panel to control actuation of the at least one drive motor, for moving the surgical instrument along at least one degree of freedom.

20. The medical robotics system of claim 19, wherein the user interface is a touchscreen device configured to actuate the at least one drive motor in response to at least one of:
 one finger pressing and holding an activation surface portion of the touchscreen device and another finger simultaneously operating the touchscreen device;
 at least two fingers simultaneously operating the touchscreen device;
 a double finger tap preceding operation of the touchscreen device; and
 at least two fingers alternating contact with at least two spaced apart portions of the touch screen device.

* * * * *